United States Patent
Weldon et al.

(10) Patent No.: US 11,617,496 B2
(45) Date of Patent: Apr. 4, 2023

(54) MEDICAL DEVICES AND RELATED METHODS

(71) Applicant: Boston Scientific Scimed, Inc., Maple Grove, MN (US)

(72) Inventors: James Weldon, Newton, MA (US); Scott E. Brechbiel, Acton, MA (US); Evan Wilder, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 344 days.

(21) Appl. No.: 16/823,633

(22) Filed: Mar. 19, 2020

(65) Prior Publication Data
US 2020/0297190 A1    Sep. 24, 2020

Related U.S. Application Data

(60) Provisional application No. 62/821,060, filed on Mar. 20, 2019.

(51) Int. Cl.
*A61B 1/00*    (2006.01)

(52) U.S. Cl.
CPC ...... *A61B 1/00087* (2013.01); *A61B 1/00094* (2013.01); *A61B 1/00096* (2013.01);
(Continued)

(58) Field of Classification Search
CPC ............ A61B 1/00087; A61B 1/00094; A61B 1/00096; A61B 1/00121; A61B 1/00137;
(Continued)

(56) References Cited

U.S. PATENT DOCUMENTS 4,706,671 A * 11/1987 Weinrib ............ A61M 25/0068
                                                         606/159
5,976,073 A * 11/1999 Ouchi ................ A61B 1/00089
                                                         600/156
(Continued)

FOREIGN PATENT DOCUMENTS

WO    WO 2014/151938 A2    9/2014

OTHER PUBLICATIONS

International Search Report and Written Opinion of the International Search Authority dated May 28, 2020, issued in corresponding International Application No. PCT/US2020/023516, filed Mar. 19, 2020 (13 pages).

*Primary Examiner* — Timothy J Neal
*Assistant Examiner* — Sung Ham
(74) *Attorney, Agent, or Firm* — Bookoff McAndrews, PLLC

(57) ABSTRACT

According to one aspect, a medical device may be configured for use with an endoscope and may include a tool. The tool may include an actuator, at least one extension at a distal portion of the actuator, and a distal end. The at least one extension may extend radially outward from the actuator and may have an edge configured to fragment debris within a body. The medical device may also include a cap configured for coupling to a distal end of the endoscope, and the cap may include a body defining an opening and a cavity. The opening may be configured to align with optics of the endoscope, and the at least one extension may be positioned within the cavity of the body.

15 Claims, 5 Drawing Sheets

(52) U.S. Cl.
CPC ...... *A61B 1/00121* (2013.01); *A61B 1/00137* (2013.01); *A61B 1/00082* (2013.01); *A61B 1/00085* (2013.01)

(58) Field of Classification Search
CPC ............ A61B 1/00082; A61B 1/00085; A61B 17/221; A61B 2017/00269; A61B 2017/00296; A61B 1/00089; A61B 1/00101; A61B 1/015; A61B 17/320783; A61B 2017/320024; A61B 2017/320775; A61B 17/32002
USPC .................................................. 600/129, 156
See application file for complete search history.

(56) References Cited

U.S. PATENT DOCUMENTS

| | | | |
|---|---|---|---|
| 6,059,719 A | 5/2000 | Yamamoto et al. | |
| 6,206,900 B1* | 3/2001 | Tabatabaei | A61B 17/320758 606/180 |
| 2002/0058904 A1* | 5/2002 | Boock | A61B 17/320783 604/35 |
| 2003/0009085 A1* | 1/2003 | Arai | A61B 1/00089 600/127 |
| 2010/0063353 A1 | 3/2010 | Eliachar et al. | |
| 2016/0338681 A1 | 11/2016 | Smith et al. | |
| 2017/0087284 A1 | 3/2017 | Shtul | |
| 2019/0274702 A1* | 9/2019 | Sutliff, III | A61B 1/015 |

* cited by examiner

MEDICAL DEVICES AND RELATED METHODS

CROSS-REFERENCE TO RELATED APPLICATIONS

This application claims the benefit of priority from U.S. Provisional Application No. 62/821,060, filed Mar. 20, 2019, which is incorporated by reference herein in its entirety.

TECHNICAL FIELD

Various aspects of the present disclosure relate generally to endoscopic devices. More specifically, embodiments of the present disclosure relate to endoscopic devices for disrupting, fragmenting, and/or removing tissue or other debris from of a patient's body and related methods of use, among other aspects.

BACKGROUND

During endoscopic procedures, the presence of a blood clot, a tissue formation, or other debris may obstruct the view of an endoscopic camera and may prevent the visualization or identification of a target area within a patient's body. For example, a procedure to stop the bleeding of an area of injured tissue may require the removal of a clot, tissue, or other debris prior to hemostasis. In some cases, physicians may spend the majority of the procedure time evacuating blood, clot, or other debris from the patient's anatomy prior to hemostasis.

Depending on the size of the tissue, a snare or basket may be used to break the clot and allow for the clot's removal. While some pieces of clot may be small enough to remove through a working channel of an endoscope, larger pieces of clot may require removal of the entire endoscope while holding the large piece of clot at the distal tip of the endoscope with a basket or snare. For example, the removal of large clots may require the physician to remove and reintroduce an endoscope several times during a procedure. Repeated removal and reintroduction of an endoscope during a procedure should be minimized, as this may slow the procedure time, frustrate the physician, and cause trauma to the patient. Even when a blood clot doesn't require breaking, clearing a clot and associated blood using a vacuum capability of an endoscope can take a significant amount of time. Current endoscope tissue removal systems often include use of suction through a working channel extending through an endoscope and the endoscope's umbilicus, which may result in low or insufficient suction flow rate.

When a distal end of an endoscope is positioned proximate to bleeding tissue, the suctioning of the blood can create a cloud of red within the field of view of the endoscope's camera caused by the movement of blood. Such an occurrence is often referred to as "red-out" conditions, and impairs the field of view of the physician during a procedure. This potential visual impairment introduces a level of unpredictability for the physician performing the procedure and potential risk for the patient.

SUMMARY

Aspects of the disclosure relate to, among other things, systems, devices, and methods for disrupting, fragmenting, and/or removing tissue or other debris from a body. Each of the aspects disclosed herein may include one or more of the features described in connection with any of the other disclosed aspects.

According to one aspect, a medical device may be configured for use with an endoscope and may include a tool. The tool may include an actuator, at least one extension at a distal portion of the actuator, and a distal end. The at least one extension may extend radially outward from the actuator and may have an edge configured to fragment debris within a body. The medical device may also include a cap configured for coupling to a distal end of the endoscope, and the cap may include a body defining an opening and a cavity. The opening may be configured to align with optics of the endoscope, and the at least one extension may be positioned within the cavity of the body.

In other aspects of this disclosure, the medical device may include one or more of the features below. The device may include a tube defining a lumen housing the actuator of the tool, and the lumen may be in fluid communication with the cavity of the body of the cap. The cap may be integral with the tube. The opening of the cap may extend from a proximal end of the cap to a distal end of the cap. The at least one extension may be helically-shaped, tear-drop shaped, or arch-shaped. The at least one extension may be a plurality of wires radially spaced around the actuator. The cavity may be configured to couple to a fluid channel of the endoscope. The at least one extension of the tool may be configured to rotate within the cavity. The medical device may further include an adapter. The adapter may include a device port, a vacuum port, and a catheter port. The device port may be configured to receive the tool. The catheter port may be coupled to the tube. A distal tip of the tool may be secured within a second cavity of the cap to restrict longitudinal movement of the tool and allow rotational movement of the tool about a longitudinal axis of the tool. A second cavity of the cap may have a length permitting a range of longitudinal movement of the tool. The cap may be cylindrical, and the cavity may extend from a radially outer portion of the cap to a radially inner portion of the cap. The medical device may further include a rotatable wheel coupled to a portion of the cap. The cavity may open to a side of the cap and the opening may open to an end of the cap transverse to the side of the cap.

In other aspects, a medical device configured for use with an endoscope may include a catheter. The catheter may include a lumen, and the catheter may be configured to receive suction from a vacuum source. The medical device may also include a tool including an actuator and a distal portion. The distal portion may include at least one extension coupled to the actuator. The at least one extension may be configured to retract when positioned within a lumen and expand radially outward from a retracted state to an expanded state when exiting a lumen. The tool may be longitudinally and rotationally movable within the lumen. The at least one extension may be configured for fragmenting debris for suctioning into the lumen.

In other aspects of this disclosure, the medical device may further include one or more of the features below. An adapter may include a device port, a vacuum port, and a catheter port. The device port of the adapter may be configured to receive a tool. The catheter port may be configured to receive the proximal end of the catheter. The catheter port may be coupled to the catheter.

In other aspects of this disclosure, a medical method may include positioning a distal end of an endoscope adjacent a target area in a body lumen. The endoscope may include a working channel. The method may also include positioning a catheter within the working channel of the endoscope. The tool may include a distal portion configured to fragment debris within the body lumen. The tool may be within a lumen of the catheter. The method may further include moving a distal end of the catheter distally beyond a distal end of the working channel. The method may also include applying a vacuum source to the lumen of the catheter. The method may further include positioning the distal portion of the tool distal to the distal end of the catheter and proximate the debris. The method may further include rotating the tool about a longitudinal axis of the tool to fragment the debris via the distal portion of the tool.

In other aspects, the medical method may further include one or more of the features below. The fragmented debris may enter the lumen of the catheter when applying the vacuum source to the lumen. A proximal portion of the tool may be positioned within an adapter. The adapter may include a device port, a vacuum port, and a catheter port. The proximal portion of the tool may be positioned within the device port and the catheter port. A portion of the tool within the lumen of the catheter may be helical-shaped.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. Throughout the figures included in this application, arrows labeled "P" and "D" are used to show the proximal and distal directions in the figure. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Further, relative terms such as, for example, "about," "substantially," "approximately," etc., are used to indicate a possible variation of ±10% in a stated numeric value or range.

Embodiments of this disclosure seek to improve a physician's ability to disrupt, dislodge, fragment, collect, and/or remove tissue, clots, or other debris from a patient's body during an endoscopic procedure and help reduce the need to remove and reintroduce the endoscope into the patient's body, among other aspects.

Figure 1:
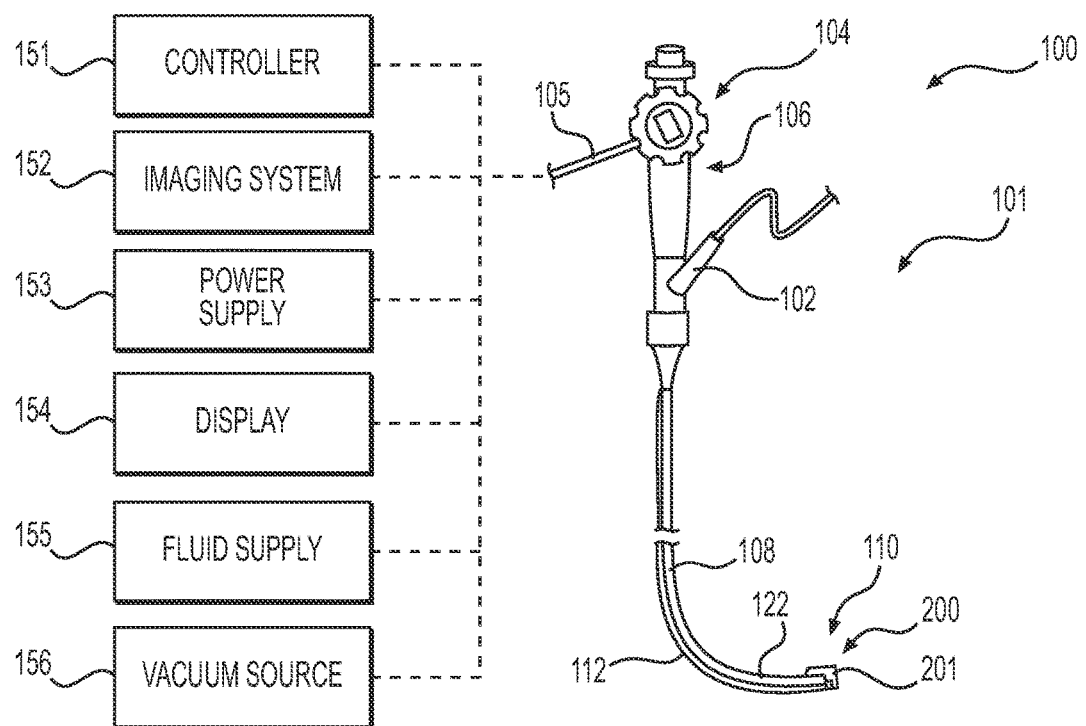
FIG. 1 is a perspective view of an endoscope system, according to aspects of this disclosure.

FIG. 1 shows a perspective view of an endoscope system 100. Endoscope system 100 may include an endoscope 101. Endoscope 101 may include a handle assembly 106 and a flexible tubular shaft 108. The handle assembly 106 may include a biopsy port 102, an actuator 104, and an umbilicus 105 may extend from handle assembly 106 to auxiliary devices. The flexibility of shaft 108 may be sufficient to allow shaft 108 to bend, to facilitate navigation of shaft 108 through a subject's tortuous anatomical passages. Shaft 108 may terminate at a distal tip 110. Shaft 108 may include an articulation section 122 for deflecting distal tip 110 in up, down, left, and/or right directions. In one example, articulation section 122 may provide for full retroflexion (e.g., rotation of distal tip 110 through an arc of 180 degrees) or only partial retroflexion (e.g., rotation of distal tip 110 through an arc of less than 180 degrees). Endoscope 101 also may include one or more lumens extending therethrough (such as lumen 215 shown in FIG. 2), and one or more openings in communication with the one or more lumens (such as opening 216 at a distal end face, shown in FIG. 3). For example, the one or more lumens may extend through handle assembly 106 and shaft 108, and the one or more openings may be on handle assembly 106 and distal tip 110.

One or more auxiliary devices may be operatively coupled to endoscope 101. Exemplary auxiliary devices may include a controller 151, an imaging system 152, a power supply 153, a display 154, a fluid supply 155, and/or a vacuum source 156, each of which is briefly described below. Controller 151 may include, for example, any electronic device capable of receiving, storing, processing, generating, and/or transmitting data according to instructions given by one or more programs. Controller 151 may be operatively coupled to, or be part of, one or more of endoscope 101 and the other auxiliary devices, to control one or more aspects of their operation. Power supply 153 may include any suitable power source, and associated connectors (e.g., electrically-conductive wires), for supplying electronic components in the auxiliary devices and endoscope 101 with electrical power. Fluid supply assembly 155 may include a reservoir, a medical irrigation bag, a pump, and any suitable connectors (e.g., tubing for fluidly coupling fluid supply 155 and endoscope 101). The pump may supply a flow of pressurized fluid to one or more of the lumens in endoscope 101, and the pressurized fluid flow may be emitted from distal tip 110. Vacuum source 156 may provide suction or vacuum pressure to one or more lumens of the endoscope or other devices, and thereby provide a suction force to draw material toward and/or into endoscope 101 or another device. Although illustrated as separate components, it is understood that all or any combination, or elements of, the controller 151, imaging system 152, power supply 153, display 154, fluid supply 154, and/or vacuum source 155 may be integrated in a single unit.

As shown in FIG. 1, endoscope system 100 may further include a cap assembly 200 including a cap 201 and a catheter 112 (or other tubing) extending from the cap 201 to a proximal portion of endoscope system 100. Catheter 112 may be coupled to fluid supply 155, vacuum source 156, or any other auxiliary device. In some examples, catheter 112 may supply fluid to the distal tip 110 of endoscope 101 or to a body lumen adjacent tip 110. In other examples, catheter 112 may supply suction at the distal tip 110 of endoscope 101 and to areas adjacent tip 110. Cap 201 may be removable from distal tip 110 of endoscope 101. Cap 201 also may be integral with or removable from catheter 112.

Figure 2:
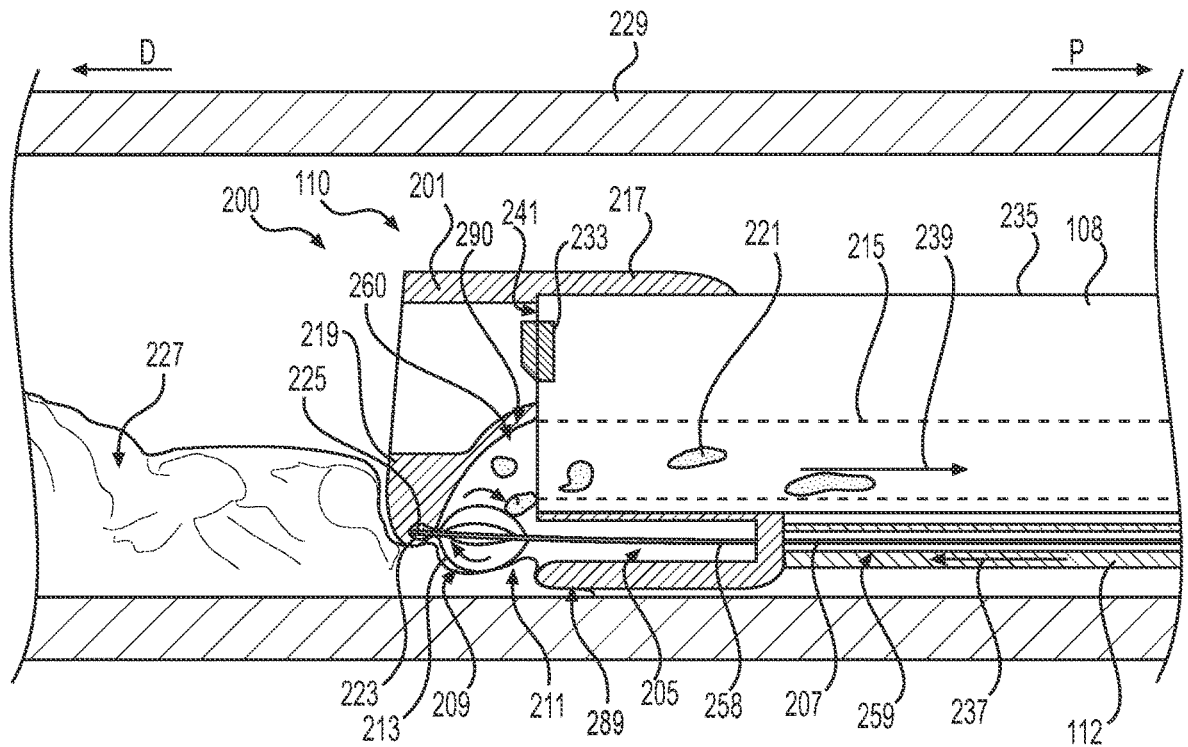
FIG. 2 is a side cross-sectional view of a distal end of an endoscope system, according to aspects of this disclosure.

FIG. 2 shows an exemplary distal tip 110 including cap assembly 200 positioned within a body lumen 229. Cap 201 or cap assembly 200 may be positioned over the distal front face 241 of endoscope 101 with portions of the cap 201 extending adjacent to a distal portion of the radially outer surface 235 of shaft 108 to couple cap 201 to distal tip 110. Cap 201 may couple to tip 110 and shaft 108 through any suitable method, including a snap fit, friction fit, or other means. Cap 201 may include a distal opening 205 in fluid communication with a lumen extending through catheter 112. Opening 205 opens into a gap portion 211 of cap 201. Gap portion 211 extends between a distal portion 219 of cap 201 and opening 205. Distal portion 219 may extend from the distal front face 241 of endoscope 108 and may align with opening 216 (shown in FIG. 3) to form a channel 260 from opening 216 to gap portion 211. Channel 260 may extend from a radially outer portion 289 of the cap 201 to a radially inner portion 290 of the cap 201. Distal portion 219 may provide a window or opening 251 (shown in FIG. 3) to allow a user to visualize the area in front of the endoscope 108, for example by using image sensor 233 positioned on the distal front face 241 of endoscope 108. A circumferential portion 217 of cap 201 may be configured to be positioned around the radially outer surface 235 of endoscope 108 and may be circular. A portion of the circumferential portion 217 may define opening 205.

Catheter 112 may extend from the portion of cap 201 defining distal opening 205 proximally and adjacent to the exterior surface 235 of endoscope 108. Catheter 112 may include a lumen 259 extending from and in communication with distal opening 205 to a proximal portion of catheter 112. Lumen 259 may be configured to receive a tool 207 and may be coupled to a fluid supply 155 or a vacuum source 156 at its proximal end. In some examples, an exterior portion of catheter 112 may be coupled to the radially outer surface 235 of endoscope 108. In other examples, catheter 112 may be spaced from the radially outer surface 235 of catheter 112. Flow direction indicator 237 shows the direction of travel of fluid through the catheter 112 towards opening 205. In other examples, the direction of travel of fluid may be reversed if suction is applied.

Tool 207 may extend from a proximal portion of catheter 112 through lumen 259 to a distal end 225. Tool 207 may include an elongate member/actuator 258, a distal end/tip 225, and a blender portion 209. Actuator 258 may be cylindrical (e.g. a wire, a rod, a cable, etc.) and may be configured to rotate about its longitudinal axis. The distal end or tip 225 of tool 207 may be positioned in a pocket or cavity 223 in distal portion 219 of cap 201 to prevent longitudinal movement of distal end 225 but allow its rotation. Distal end 225 may be fixed or coupled to a portion of cavity 223, for example such that tool 207 may rotate about its longitudinal axis and is prevented from moving proximally or distally. In some examples, distal end 225 may include a spherical tip that is received by cavity 223 and the spherical tip may prevent the distal end 225 from moving out of cavity 223. In some examples, distal end 225 may include a magnetic material and cavity 223 may also include a magnetic material such that when distal end 225 is positioned within cavity 223, distal end 225 is held within cavity 223 via a magnetic force. Blender portion (or fragmentation portion) 209 is positioned on the distal end of actuator 208 and includes at least one extension 213 extending radially outward from actuator 208. As shown in FIG. 2, several extensions 213 may extend radially outward from actuator 258 at a distal portion of tool 207, may be arch-shaped, and may be coupled to body 258 at two points. In some examples, arch-shaped extensions 213 may be configured to extend within opening 211 to facilitate breaking apart clot 227. In other examples, extensions 213 may include rectangular-shaped paddles extending outward from actuator 258. In some examples, extensions 213 may together form a basket or cage-like shape. The extensions 213 may be a shape-formed metal/alloy, such as nitinol. In some examples, extensions 213 may include sharp edges along their length for cutting debris. In other examples, extensions 213 may not include sharp edges and/or may include wire portions without sharp edges, yet are still configured to cut tissue. Tool 207 may be positioned in catheter 112 such that a user may manually rotate tool 207 at its proximal end about its longitudinal axis to rotate blender portion 209. In other examples, a user may use a motor or any other torque driver known in the art to rotate the proximal portion of tool 207.

Figure 3:
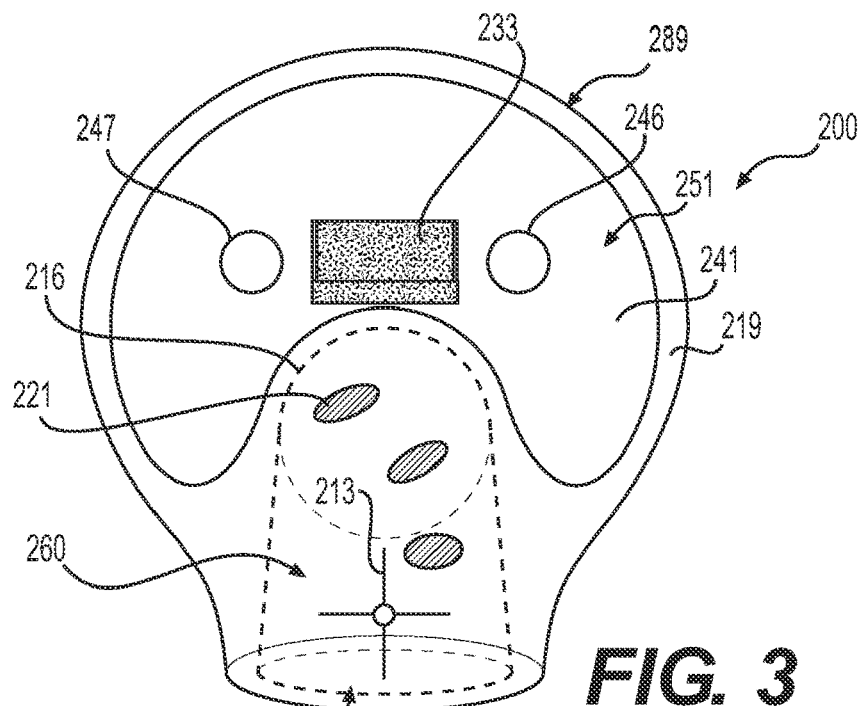
FIG. 3 is a front view of the distal end of the endoscope system of FIG. 2, according to aspects of this disclosure.

FIG. 3 shows a front view of the cap assembly 200 shown in FIG. 2 and the distal face 241 of endoscope 108. Opening 251 of cap 201 may allow an image sensor 233 at the distal front face 241 of endoscope 108 to view the area in front of or distal to the cap 201, and allow illuminators 246, 247 to illuminate the field of view of image sensor 233. As shown in FIGS. 2 and 3, cap 201 may be configured to align with an opening 216 of a lumen 215 of endoscope 108. When suction is applied to lumen 215 (for example, via vacuum source 156), clot 227 may be pulled towards opening 211 and channel 260. As clot 227 is positioned in opening 211 due to suction applied to lumen 215, blender portion 209 may assist in breaking apart clot 227 to allow fragments of clot 227 to travel through lumen 215. A user may rotate tool 207 to spin blender portion 209, including extensions 213, to break clot 227 into smaller pieces. By rotating tool 207 and breaking apart clot 227 with blender portion 209, a user may prevent clogging of opening 216 when suction is applied to lumen 215. For example, FIG. 2 shows endoscope 108 with cap assembly 200 positioned within a body lumen 229 and clot 227 pulled towards opening 211 via a suction force (shown in arrow 239) from lumen 215. After clot 227 contacts extensions 213 of blender portion 209, clot 227 is broken into smaller pieces 221 to facilitate transporting it through channel 260 and lumen 215. By forcing clot 227 to travel through opening 211 and toward blender portion 209 using a suction force from lumen 215, cap assembly 200 facilitates the breaking apart of clot 227 and its removal from a patient. In some examples, distal end 225 of tool 207 may be moved longitudinally in the proximal and distal directions, into and out of cavity 223, to facilitate breaking apart clot 227. For example, cavity 223 can be longer than end 225, so that end 225 has a range of movement therein without end 225 exiting cavity 223. In some examples, tool 207 may be removed from cavity 223 and allowed to move freely within opening 211.

Figure 4A:
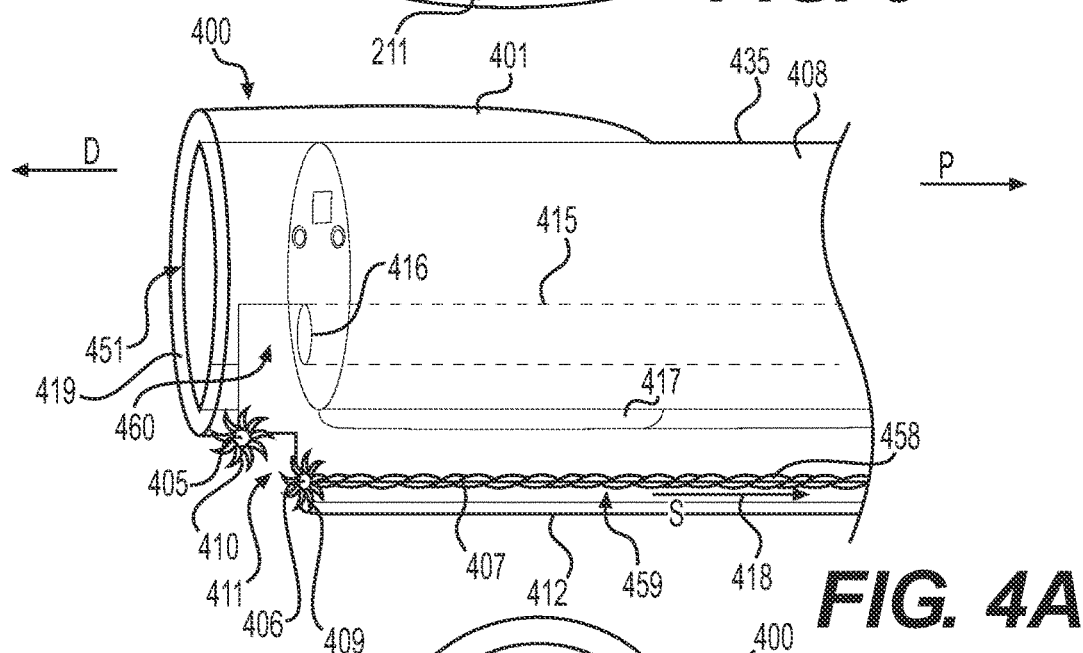
FIGS. 4A and 4B are side and front views, respectively, of a distal end of an endoscope system, according to aspects of this disclosure.
Figure 4B:
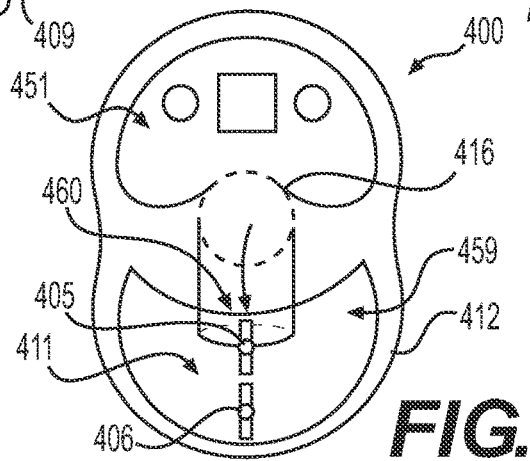

FIGS. 4A and 4B show an alternative embodiment of a cap assembly 400 similar to the cap assembly 200 described above. Cap assembly 400 may include cap 401, distal portion 419 of cap 401, catheter 412, opening 451, channel 460, and tool 407, which may include any of the features described above with regard to cap assembly 200. A proximal portion 417 of cap 401 may extend circumferentially around a radially outer surface 435 of an endoscope 408 and may be configured to couple cap assembly 400 to endoscope 408. Channel 460 of cap 401 may be configured to align with an opening 416 of lumen 415 of endoscope 408. Channel 460 may connect opening 411 to lumen opening 416. Tool 407 may extend from a proximal portion of catheter 412 to opening 411 at the distal end of catheter 412. In some examples, tool 407 may include a paddle wheel 406 at its distal end that is positioned within a portion of opening 411 at the distal end of catheter 412. Paddle wheel 406 may include radial extensions 409 that are configured to rotate when actuator 458 of tool 407 is rotated about its longitudinal axis. Radial extensions 409 may extend perpendicular to the central longitudinal axis of tool 407. In some examples, radial extensions may extend transverse to the longitudinal axis of tool 407. In other examples, radial extensions 409 may be fixedly coupled to a rotatable inner hub (or pulley), which rotates about an axis transverse (e.g. perpendicular) to the longitudinal axis of tool 407, and relative to a proximal portion of tool 407. A cable may extend from the rotatable inner hub (e.g. around a pulley) to a proximal portion of tool 407. In this example, a user may pull the cable proximally to rotate the inner hub and thus rotate paddle wheel 406. In some examples, tool 407 may include a gear at the distal end that rotates as tool 407 is rotated about its axis. That gear engages gearing on paddle wheel 406 such that when a user rotates tool 407 about its longitudinal axis, paddle wheel 406 is rotated about an axis transverse to the longitudinal axis of tool 407. In other examples, paddle wheel 406 may be rotated 90 degrees from its position shown in FIGS. 4A and 4B, so that it rotates in the plane of FIG. 4B. Rotation of tool 407 about its axis will rotate wheel 406 in that plane. Radial extensions 409 may be sharp and may be configured to cut tissue. In some examples, when radial extensions 409 are sharp and configured to cut tissue, paddle wheel 406 may be positioned in cap assembly 400 to prevent unwanted contact between paddle wheel 406 and healthy tissue. For example, paddle wheel 406 may be positioned within lumen 459 such that radial extensions 409 do not extend beyond the radially outer surface of catheter 412, which may help avoid unwanted contact between radial extensions 409 and healthy tissue. The rotation of wheel 406 may cut or otherwise separate tissue, clot, or other debris and also force such debris into channel 460 through its direction of rotation. In some examples, distal portion 419 of cap 410 may include a second paddle wheel 405 with radial extensions 410. Second paddle wheel 405 may be coupled to distal portion 419 such that paddle wheel 405 may rotate freely. For example, wheel 405 may be mounted to portion 419 via an axle pin and bearing, allowing free rotation of wheel 405. Opening 411 may extend between paddle wheel 405 and paddle wheel 406.

FIG. 4B shows a front view of cap assembly 400 including lumen opening 416, channel 460, opening 451, paddle wheels 405, 406, catheter 412, and opening 411. In some examples, lumen 459 of catheter 412 may have a non-circular circumference such as the partially circular circumference (causing a moon-shaped cross-section) shown in FIG. 4B. In other examples, lumen 459 may have a circular circumference. As shown in FIG. 4B, paddle wheels 405, 406 may be vertically spaced from each other forming a space between them within opening 411 for debris to travel. In some examples (not shown), paddle wheels 405, 406 may be positioned so that radial extensions 409, 410 are staggered or spaced apart relative to a longitudinal axis of cap assembly and/or endoscope 408. Paddle wheel 405 may be vertically aligned with paddle wheel 406 and spaced such that both paddle wheel 405 and paddle wheel 406 may rotate freely without touching each other. Paddle wheels 405, 406 may be positioned at the center portion of opening 411 and may be aligned with channel 460. In other examples, paddle wheels 405, 406 may be horizontally aligned or may have any other orientation relative to each other while being positioned within opening 411. In some examples, the device may only include paddle wheel 406 or only include paddle wheel 405.

Lumen 459 may be coupled to a vacuum source 156 to provide suction in a distal-to-proximal direction (shown by suction arrow 418) through lumen 459 and at opening 411. During operation, in some examples, a user may apply suction to lumen 459 to pull tissue, a clot, or other debris towards opening 411 and paddle wheels 405, 406. The user may then rotate body 458 of tool 407 about its longitudinal axis to rotate paddle wheel 406, which may cause extensions 409 to contact and break apart debris that has gathered proximal to opening 411 and allow such debris to travel through lumen 459. In other examples, the user may pull a wire to actuate a pulley mechanism to rotate paddle wheel 406. Paddle wheel 405 may also facilitate breaking apart debris. For example, the suction force applied through lumen 459 may cause rotation of wheel 405, further fragmenting debris. To facilitate breaking apart and dislodging debris, the user may supply fluid through lumen 415 of endoscope, which may travel through channel 460 and through opening 411. In other examples, liquid may be supplied through lumen 458 and suction may be applied to lumen 415, causing fragmented tissue to be removed through lumen 415. Supplying liquid to channel 460 and opening 411 may facilitate in breaking apart debris. After use, cap assembly 400 may be removed from endoscope 408 and may be used on a different endoscope.

Figure 5A:
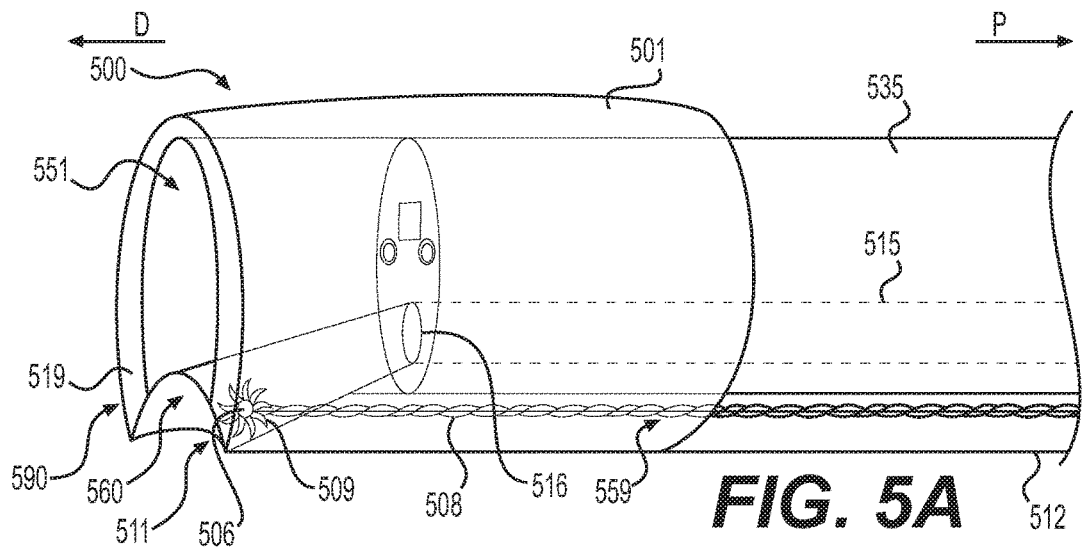
FIGS. 5A and 5B are side and partial side views, respectively, of a distal end of an endoscope system, according to aspects of this disclosure.

FIG. 5A shows an alternative embodiment of a cap assembly 500 including cap 501 with distal portion 519, channel 560, tool 508 including paddle wheel 506 with extensions 509, opening 511, catheter 512, lumen 559, and opening 551. Any of the components of cap assembly 500 may include any of the features described above with regard to cap assemblies 200 and 400. In cap 501, channel 560 extends from an opening 516 of a lumen 515 of endoscope 535 to the distal front face 590 of cap 501 and the side of cap 501. By extending channel 560 from the distal end of endoscope 535, paddle wheel 506 is positioned farther from the distal end of endoscope 535 and may prevent debris from contacting the distal end of endoscope 535. Channel 560 of cap 501 may be cylindrical and may extend linearly from opening 516 to the distal front face 590 and side of cap 501. By providing a linear channel 560, cap assembly 500 may prevent build up of tissue within channel 560 that may otherwise be caused by curves or bends in a channel wall.

Channel 560 may be angled such that the proximal end of channel 560 is positioned at a radially-outer portion of distal portion 519.

Figure 5B:
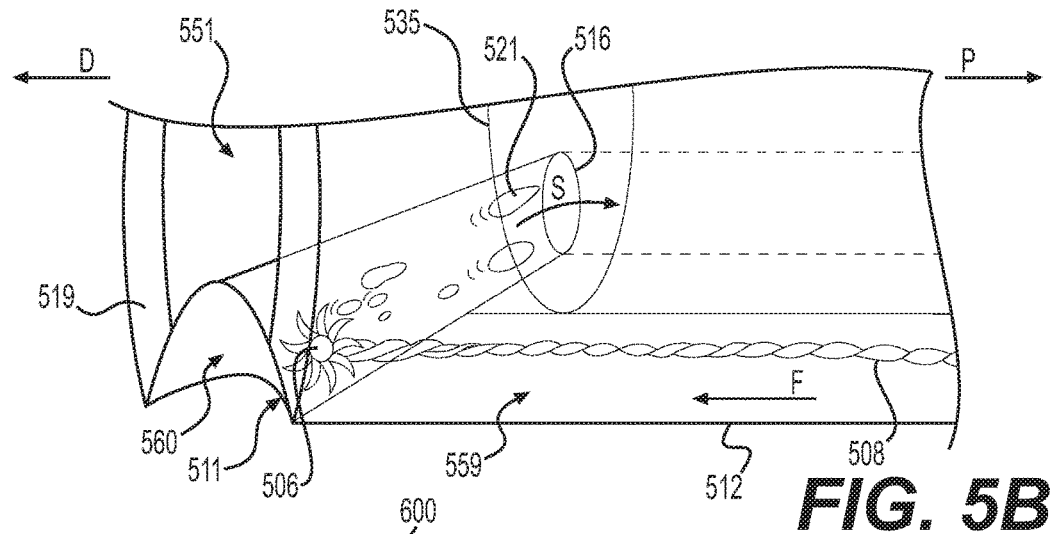

FIG. 5B shows a magnified view of channel 560 of cap 501 with fragmented debris 521 (e.g. tissue or clot) traveling through channel 560 towards opening 516. In some examples, a user may supply fluid through lumen 559 (shown by fluid arrow F in FIG. 5B) to opening 511 and channel 560, which may facilitate breaking apart and/or dislodging debris. Suction may be applied to lumen 515 and opening 516 (shown by suction arrow S in FIG. 5B) to facilitate collecting debris at opening 511 and moving fragmented debris through channel 560 and lumen 515.

Figure 6:
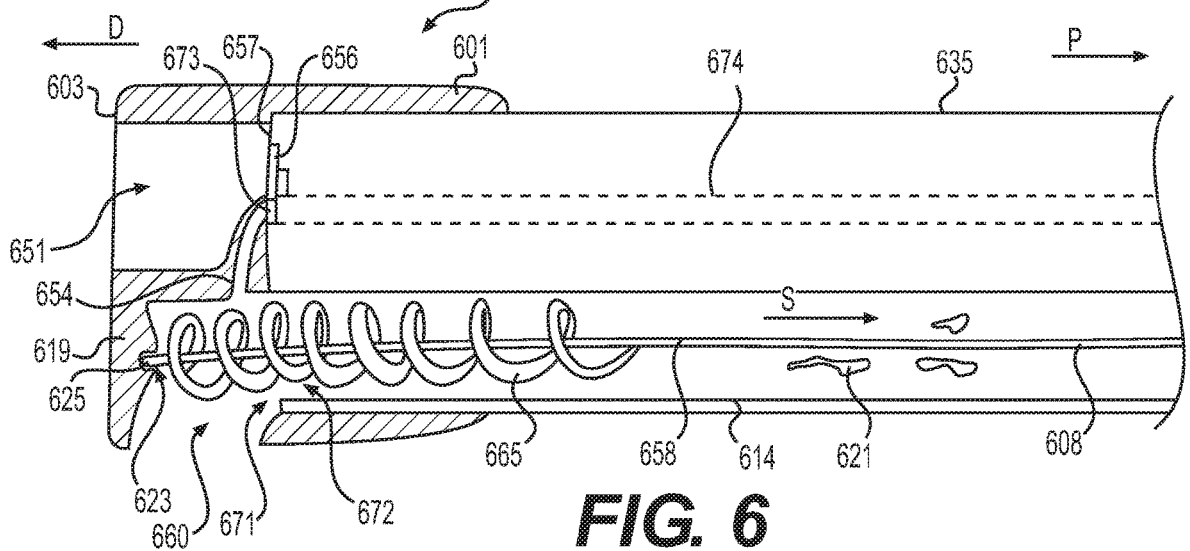
FIG. 6 is a side cross-sectional view of a distal end of an endoscope system, according to aspects of this disclosure.

FIG. 6 shows an alternative embodiment of a cap assembly 600 utilizing a working channel 614 of an endoscope 635. Any of the components of cap assembly 600 may include any of the features described above with regard to cap assemblies 200 and 400. Cap assembly 600 positions tool 608 within a working channel 614 of endoscope 635 instead of a catheter used in previously described embodiments of cap assemblies. Channel 654 of cap 601 may align with an opening 673 of a fluid lumen 674 of endoscope 635. A distal front face 657 of endoscope 635 may abut cap 601 and a distal front surface 603 of cap may be parallel to the distal front face 657 of endoscope 635. In other examples, channel 654 may align with any type of lumen of an endoscope. Channel 654 may be configured to receive fluid from fluid lumen 671 and direct fluid towards a distal portion of tool 608. Cap 601 may also include an opening 671 in fluid communication with channel 660 and aligned with the distal opening 672 of working channel 614. A cavity 623 in a distal portion 619 of cap 601 may be longitudinally aligned with opening 671. Tool 608 may be positioned within working channel 614, and the distal end 625 of tool 608 may be positioned within cavity 623, which may prevent tool 608 from translating distally and allow tool 608 to rotate about its longitudinal axis (much like the embodiment shown and described in FIGS. 2A and 2B). Any of the coupling means described hereinabove in connection with distal end 219 and cavity 223 may be used to couple distal end 625 to cavity 623. The positioning of distal end 625 of tool 608 within cavity 623 may assist with maintaining the position of tool 608 within working channel 614.

As shown in FIG. 6, tool 608 may include an extension 665 at a distal section of tool 608. Extension 665 may be cylindrical and may be in the shape of a helix. Extension 665 may be coupled to a cylindrical body (or longitudinal actuator) 658 of tool 608 at distal and proximal ends of extension 665. Tool 608 is much like an auger, therefore when rotating tool 608 about its longitudinal axis, extension 665 may provide a means to move debris 621 in a distal to proximal direction through working channel 614 to assist with debris removal. In some examples, extension 665 may include sharp edges to fragment debris. In some examples, a user may disengage the distal portion 625 of tool 608 from cavity 623 to move tool 608 proximally and move any tissue coupled to tool 608, for example coupled to extension 665, proximally through working channel 614. By providing a channel 660 in which suction and/or liquid is applied that is separate from the opening 651 providing a field of view for the endoscope's image sensor 656, cap assembly 600 may facilitate maintaining a clear field of view for image sensor 656 by not applying suction or fluid directly into the field of view of image sensor 656 or within opening 651.

Figure 7:
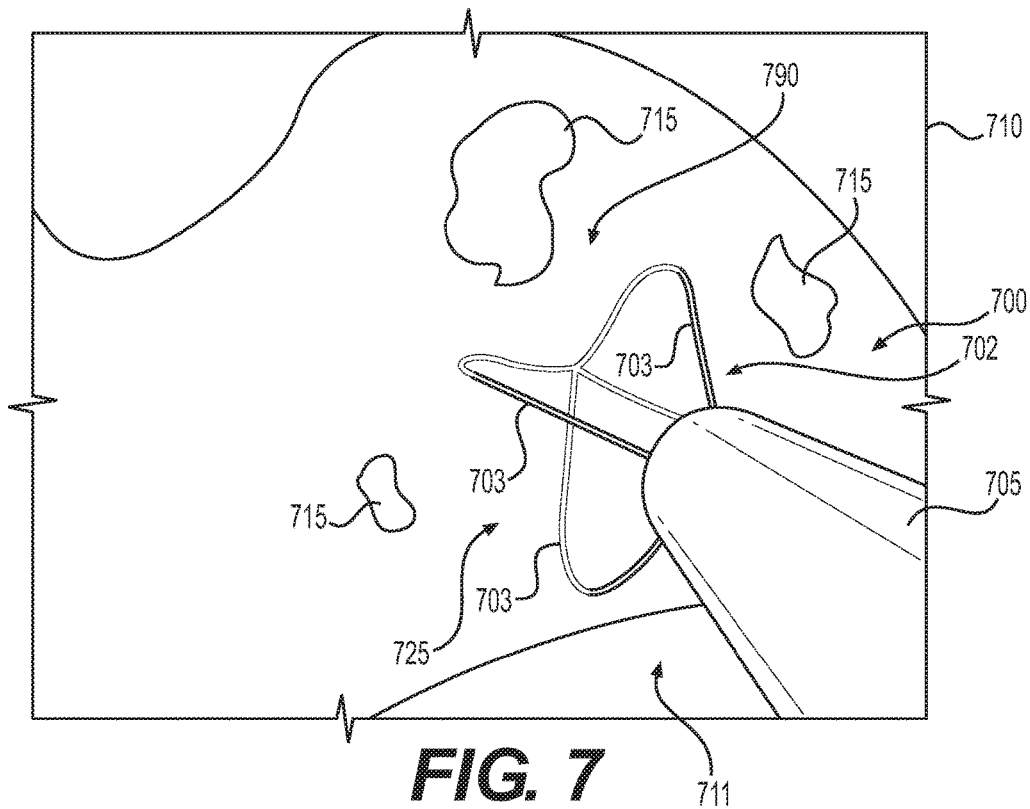
FIG. 7 is a perspective view of a field of view of an endoscope camera, according to aspects of this disclosure.

FIG. 7 shows a perspective view of a field of view 710 of an image sensor at a distal end of an endoscope positioned within a body lumen 711. The field of view 710 includes a distal portion of a tool assembly 700 positioned proximal to a target area 790 within the body lumen 711. Tool assembly 700 may include a clot-breaker tool 702 and a catheter 705. Catheter 705 may be cylindrical and may be configured to receive suction from a vacuum source 156. In some examples, catheter 705 may be sized to fit within a working channel of an endoscope and extend from a proximal portion of the endoscope, for example through a biopsy port of an endoscope, to beyond the endoscope's distal end. Clot-breaker tool 702 may extend longitudinally from a proximal portion (not shown) to a distal portion 725. Distal portion 725 may be expandable and compressible so that clot-breaker tool 702 may travel through a lumen of catheter 705 when distal portion 725 is retracted, and distal portion 725 may expand radially outward when exiting the distal end of catheter 705. In some examples, clot-breaker tool 702 may include radially-extendable portions (legs) 703 at its distal end forming a tear-drop shape similar to a balloon whisk when in an expanded state (shown in FIG. 7). The radially-extendable portions 703 may be radially compressible to a retracted state to allow portions 703 to fit within a lumen of catheter 705. In some examples, portions 703 may be biased and may have a tendency to expand radially outward into an expanded state (shown in FIG. 7).

In operation, tool assembly 700 may be positioned within a working channel of an endoscope and advanced distally from the proximal portion to beyond the distal end of an endoscope. During such insertion, distal portion 725 may be retracted with the lumen of catheter 705. Once reaching the tissue site, portions 725 may be extended from the lumen of catheter 705 to obtain its expanded configuration. Portion 725 then may be further extended to reach, for example, a clot 715. A user may apply suction to catheter 705 to pull clot 715 towards the distal end of catheter 705. A user then may rotate clot-breaker tool 702 about its longitudinal axis to rotate distal portion 725 to break apart clot 715. By breaking apart clot 715 with distal portion 725 of clot-breaker tool 702, the tissue may more easily pass through catheter 705 and be removed from the patient's body. Tool assembly 700 may provide a means for a user to improve visualization during suction and potentially mitigate "red-out" effects on the field of view of the endoscopic camera by applying suction beyond the area immediately in front of the distal end of the endoscope. Furthermore, since the user may advance catheter 705 beyond the distal end of an endoscope to apply suction to target fluid or debris, the user does not need to place the endoscope tip directly in target fluid or debris to apply suction to it.

Figure 8:
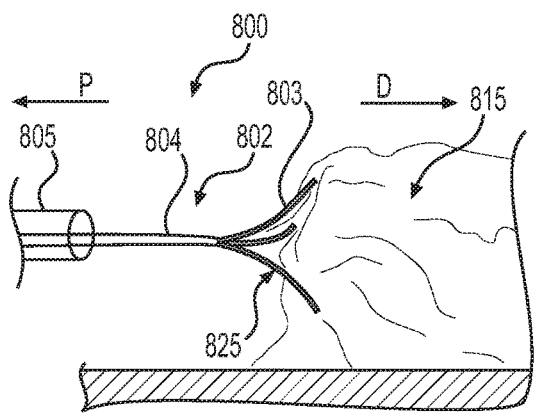
FIG. 8 is a side perspective view of a distal end of an endoscope system within a body lumen, according to aspects of this disclosure.

FIG. 8 shows an alternative embodiment of a tool assembly 800 including clot-breaker tool 802 and catheter 805. Similar to clot-breaker tool 702, clot-breaker tool 802 includes an elongate body 804 (or actuator) and a distal portion 825 including three extensions 803. In other examples, clot-breaker tool 802 may include two extensions, one extension, or greater than three extensions. Extensions 803 may be biased to expand radially outward and may be collapsible in order to fit within catheter 805. In some examples, extensions 803 may curve radially outward such that the distal end of each extension 803 is the largest distance from the longitudinal axis of body 804. The proximal end of body 804 may serve to transmit rotation applied by the user in the same manner as clot-breaker tool 704, e.g. to rotate distal portion 825 and engage extensions 803 with clot 815. In the same manner as tool assembly 700, catheter 805 may be coupled to a vacuum source at its proximal end and may apply a suction force to bring the clot or other debris towards its distal end.

Figure 9A:
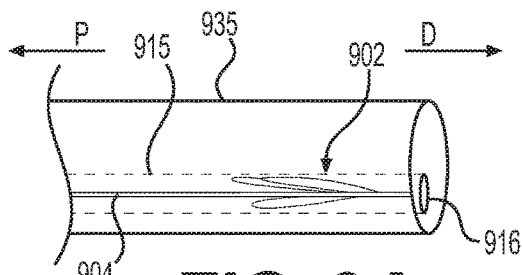
FIGS. 9A and 9B are side perspective views of a distal end of an endoscope system, according to aspects of this disclosure.
Figure 9B:
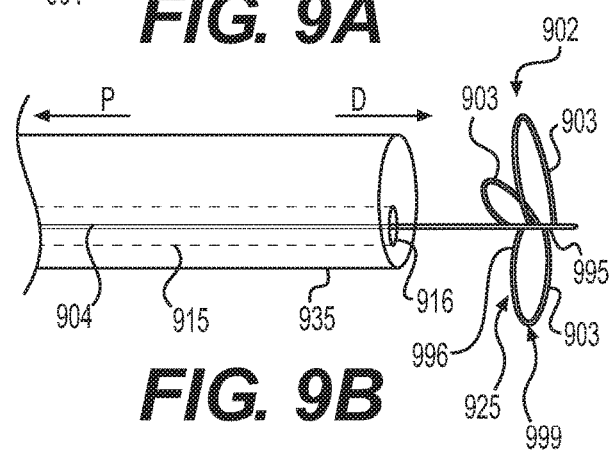

FIGS. 9A and 9B show another embodiment of a clot-breaker tool 902 in its retracted (FIG. 9A) and expanded (FIG. 9B) states and positioned within (FIG. 9A) and deployed out of (FIG. 9B) a working channel 915 of an endoscope 935. In FIG. 9A, clot-breaker tool 902 is retracted and its distal portion 925 is folded such that extensions 903 are lying adjacent to elongate body (or actuator) 904. Distal portion 925 may be biased to radially expand such that extensions 903 expand radially outward from body 904 when clot-breaker tool 902 exits the distal opening 916 of working channel 915. When positioned within working channel 915, extensions 903 of clot-breaker tool 902 may be held in a retracted state by the interior surface of working channel 915. In some examples, extensions 903 form a flower-shape configuration at distal portion 925 when in an expanded state. Each extension 903 may be in the shape of an arch extending from a first end 995 attached to body 904, radially outward from the longitudinal axis of body 904 to a peak 999, and then to a second end 996 attached to body 904. In some examples, each extension 903 may form a loop shape. In some examples, extensions 903 may be evenly spaced around the circumference of body 904. Any of the extensions 703, 803, 903 described herein may include sharp edges to aid in breaking apart debris. Any of the clot-breaker tools described herein may be utilized in a working channel of an endoscope in the same manner shown in FIGS. 9A and 9B.

Figure 10:
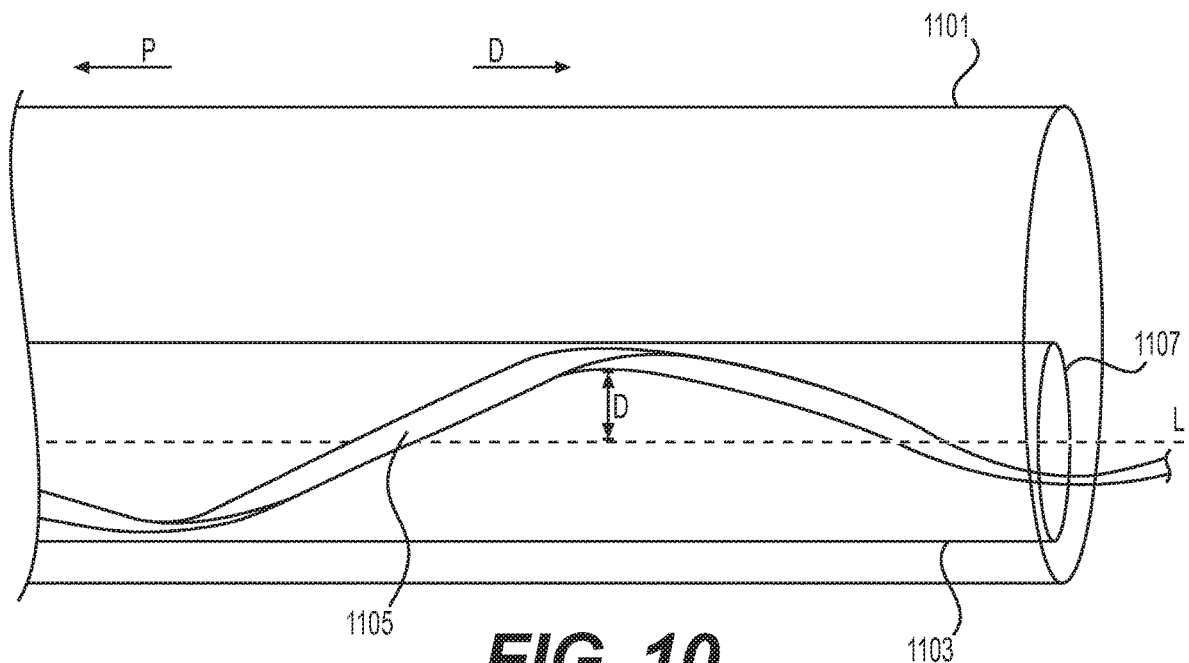
FIG. 10 is a side view of a distal end of an endoscope system, according to aspects of this disclosure.

As shown in body 1105 in FIG. 10, any of the bodies (actuators) 804, 904 of the clot-breaker tools 702, 802, 902 may be helix shaped similar to body (actuator) 1105, and may be configured to abut an interior surface 1103 of a working lumen 915, 1107 of an endoscope 1101 or catheter 705, 805. When body 1105 of a clot-breaker tool 702, 802, 902 is helical, a larger unobstructed space is available along the central longitudinal axis L within the working lumen 1107 (or within a lumen of a catheter) for tissue to travel through, which may help prevent clogging of tissue and may allow for smoother flow of tissue through the catheter or working channel 1107. The helical radius of body 1105 (shown as D in FIG. 10) may be approximately equal to the radius of a catheter lumen or working channel 1107. In some examples, the coiled or "wavy" shape, such as the shape of body 1105, may break up clot or debris along the length of a catheter as the tool, such as body 1105, rotates.

Any of the clot-breaker tools 602, 702, 802, 902 and/or distal portions 625, 725, 825, 925 may be a coil, spring, or ribbon, and may include stainless steel, nitinol, a flexible polymer, or other material with shape memory characteristics.

Figure 11:
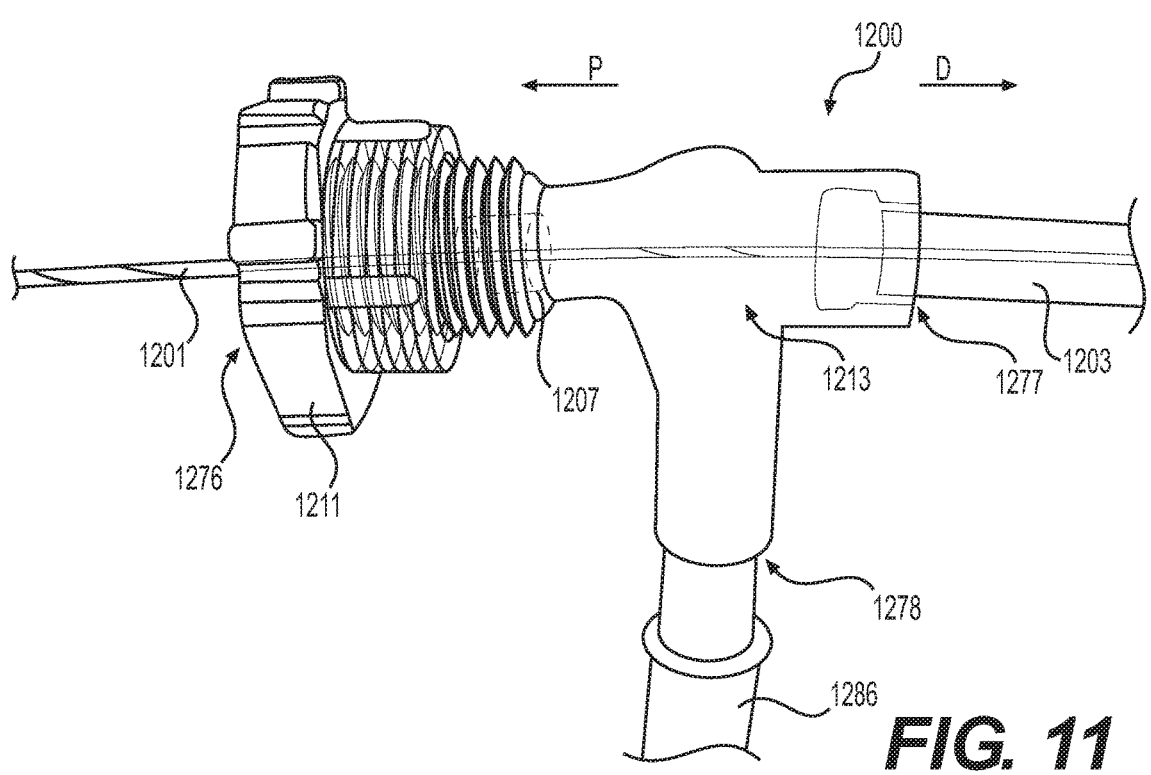
FIG. 11 is a side view of a suction adapter of an endoscope system, according to aspects of this disclosure.

When using an assembly including a clot-breaker tool and catheter, such as those described hereinabove, a user may apply suction to the catheter separate from an endoscope handle assembly 106, such as when a catheter and clot-breaker tool are inserted into an endoscope 101 through a biopsy port 102. FIG. 11 shows an exemplary adapter 1200 coupled to a proximal end of a catheter 1203 and a vacuum source connector 1286. In some examples, adapter 1200 may be T-shaped and may include a device port 1276, a catheter port 1277, and a vacuum port 1278. Clot-breaker tool 1201 may be inserted through device port 1276, through a gasket 1207 and a chamber 1213 of adapter 1200, and into catheter 1203. In some examples, the device port 1276 and the catheter port 1277 may be longitudinally aligned to facilitate the insertion of clot-breaker tool 1201. Gasket 1207 may be tightened around the proximal end of clot-breaker tool 1201 to prevent the flow of fluid though gasket 1207 (especially during application of suction) while allowing clot-breaker tool 1201 to rotate about its longitudinal axis. In some examples, gasket 1207 may be tightened by rotating cap 1211. A vacuum source 1286 may be coupled to the vacuum port 1278 to provide fluid flow, such as suctioning air, to adapter 1200. Adapter 1200 may provide a means for the user to control the vacuum source separate from an endoscope handle assembly 106.

Each of the aforementioned tool assemblies including a clot-breaker tool and a catheter, whether used in conjunction with an endoscope, tool, or any other medical device, may be used to disrupt, collect, reposition, break apart, or remove tissue, clot, or other debris. As shown in FIG. 7, the user may locate a target area 790 (such as a clot or other tissue) present in a body lumen 711 of a subject using an endoscope 101, by directly visualizing the target area 790 using an image sensor. The distal end of the catheter may be positioned proximal to the target area 790 and distal to the distal tip 110 of endoscope 101. The user may then move the clot-breaker tool distally to deploy the distal portion of the clot-breaker tool from the distal end of the catheter, which may cause a distal portion of the clot breaker tool to expand radially outward from the longitudinal axis of the clot-breaker tool (shown in FIG. 7). Once a distal portion of the clot-breaker tool is deployed beyond the distal end of catheter and proximate to tissue, the user may rotate a proximal portion of the clot-breaker tool to cause rotation of the distal portion of the clot breaker tool in order to break apart and/or dislodge tissue. In some examples, the user may simultaneously activate fluid flow through catheter to provide a suction force at the distal end of catheter to pull tissue towards the catheter's distal opening. The user may also move the clot-breaker tool proximally and distally during use to dislodge and/or break apart tissue or other debris. Additionally or alternatively, the user may remove tissue from the target area by suctioning the tissue through the catheter.

The flow rate of clot removal (Q) is governed by the radius (R) and length (L) of the working channel and vacuum tubing assembly of the endoscope system, the pressure differential (ΔP) applied by the vacuum, and the viscosity (μ) of the fluid being evacuated (according to the Darcy-Weisbach equation $$Q = \frac{\Delta P \pi R^4}{8\mu L}).$$

When holding other variables constant, the flow rate of clot removal can be increased linearly by decreasing the length of the working channel. Embodiments of the present disclosure allow for a shorter working channel and vacuum tubing assembly (e.g. catheter coupled to a vacuum source) by allowing the vacuum tubing to be inserted through a biopsy port of an endoscope system, shortening the overall length of the vacuum tubing assembly.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and embodiments be considered as exemplary only.

We claim:

1. A medical device configured for use with an endoscope, comprising:
   a tool having an actuator and at least one extension at a distal portion of the actuator, and a distal end, wherein the at least one extension extends radially outward from the actuator and has an edge configured to fragment debris within a body; and
   a cap configured for coupling to a distal end of the endoscope, the cap including a body defining an opening and a channel;
   wherein the opening is configured to align with optics of the endoscope, and the at least one extension is positioned within the channel of the body;
   wherein a distal tip of the tool is secured within a cavity of the cap to restrict longitudinal movement of the tool and allow rotational movement of the tool about a longitudinal axis of the tool.

2. The device of claim 1, further comprising a catheter defining a lumen housing the actuator of the tool, the lumen in fluid communication with the channel of the body of the cap.

3. The device of claim 2, wherein the cap is integral with the catheter.

4. The device of claim 2, further comprising an adapter, wherein the adapter includes a device port, a vacuum port, and a catheter port; wherein the device port is configured to receive the tool; and wherein the catheter port is coupled to the catheter.

5. The device of claim 1, wherein the opening of the cap extends from a proximal end of the cap to a distal end of the cap.

6. The device of claim 1, wherein the at least one extension is helically-shaped, tear-drop shaped, or arch-shaped.

7. The device of claim 1, wherein the at least one extension is a plurality of wires radially spaced around the actuator.

8. The device of claim 1, wherein the channel is configured to couple to a fluid channel of the endoscope.

9. The device of claim 1, wherein the at least one extension of the tool is configured to rotate within the channel.

10. The device of claim 1, wherein the cavity of the cap has a length permitting a range of longitudinal movement of the tool.

11. The device of claim 1, wherein the cap is cylindrical, and the channel extends from a radially outer portion of the cap to a radially inner portion of the cap.

12. The device of claim 1, wherein the channel opens to a side of the cap and the opening opens to an end of the cap transverse to the side of the cap.

13. The device of claim 1, wherein the distal tip of the tool includes a spherical tip.

14. The device of claim 13, wherein the spherical tip is positioned within the cavity.

15. The device of claim 1, where the distal tip of the tool is coupled to a portion of the cap via a magnetic material.

* * * * *